(12) United States Patent
Hansen

(10) Patent No.: US 10,668,197 B2
(45) Date of Patent: Jun. 2, 2020

(54) RESONANT POWER TRANSMISSION COILS AND SYSTEMS

(71) Applicant: TC1 LLC, St. Paul, MN (US)

(72) Inventor: John Freddy Hansen, Pleasanton, CA (US)

(73) Assignee: TC1 LLC, St. Paul, MN (US)

( * ) Notice: Subject to any disclaimer, the term of this patent is extended or adjusted under 35 U.S.C. 154(b) by 0 days.

(21) Appl. No.: 16/275,977

(22) Filed: Feb. 14, 2019

(65) Prior Publication Data

US 2019/0175809 A1 Jun. 13, 2019

Related U.S. Application Data

(63) Continuation of application No. 14/414,842, filed as application No. PCT/US2013/052551 on Jul. 29, 2013, now Pat. No. 10,251,987.
(Continued)

(51) Int. Cl.
*A61M 1/12* (2006.01)
*H02J 50/70* (2016.01)
(Continued)

(52) U.S. Cl.
CPC .......... *A61M 1/127* (2013.01); *A61N 1/3787* (2013.01); *H02J 50/10* (2016.02); *H02J 50/12* (2016.02);
(Continued)

(58) Field of Classification Search
CPC .......... H02J 5/005; H02J 7/025; A61M 1/122; A61M 2205/8243; A61N 1/378; H01F 38/14
See application file for complete search history.

(56) References Cited

U.S. PATENT DOCUMENTS

| 4,041,955 A | 8/1977 | Kelly et al. |
| 4,071,032 A | 1/1978 | Schulman |
(Continued)

FOREIGN PATENT DOCUMENTS

| DE | 202012000166 U1 | 4/2013 |
| DE | 102012201073 A1 | 7/2013 |
(Continued)

OTHER PUBLICATIONS

Bonde et al.; Promise of unrestricted mobility with innovative, portable wireless powering of a mechanical circulatory assist device; American Association for Thoracic Surgery; © 2012; 2 pgs.; retrieved Mar. 12, 2014 from the internet: http://aats.org/annualmeeting/Abstracts/2012/T8.cgi.
(Continued)

*Primary Examiner* — Rexford N Barnie
*Assistant Examiner* — Terrence R Willoughby
(74) *Attorney, Agent, or Firm* — Armstrong Teasdale LLP

(57) ABSTRACT

An improved wireless transmission system for transferring power over a distance. The system includes a transmitter generating a magnetic field and a receiver for inducing a voltage in response to the magnetic field. In various respects, the receiver is configured to be implanted in a body. The receiver may include a housing enclosing a receiving coil and associated electronic components, a covering around at least a portion of the housing, and at least two wires wrapped around the housing to form a plurality of turns. The covering may be formed of a ferrite material configured to both magnetically shield a respective portion of the internal volume of the housing and redirect incoming magnetic flux from the transmitter to improve efficiency. Methods of use are also provided.

18 Claims, 10 Drawing Sheets

Related U.S. Application Data

(60) Provisional application No. 61/676,718, filed on Jul. 27, 2012.

(51) Int. Cl.

| | | |
|---|---|---|
| *H02J 50/12* | (2016.01) | |
| *H02J 5/00* | (2016.01) | |
| *H02J 50/10* | (2016.01) | |
| *A61N 1/378* | (2006.01) | |
| *A61M 1/10* | (2006.01) | |
| *H01F 38/14* | (2006.01) | |

(52) U.S. Cl.
CPC .............. *H02J 50/70* (2016.02); *A61M 1/101* (2013.01); *A61M 1/122* (2014.02); *A61M 2205/8243* (2013.01); *H01F 38/14* (2013.01)

(56) References Cited

U.S. PATENT DOCUMENTS

| | | |
|---|---|---|
| 4,352,960 A | 10/1982 | Dormer et al. |
| 4,561,443 A | 12/1985 | Hogrefe et al. |
| 4,561,444 A | 12/1985 | Livingston et al. |
| 4,630,615 A | 12/1986 | Yomtov |
| 4,679,560 A | 7/1987 | Galbraith |
| 4,726,378 A | 2/1988 | Kaplan |
| 4,736,747 A | 4/1988 | Drake |
| 4,924,171 A | 5/1990 | Baba et al. |
| 4,945,305 A | 7/1990 | Blood |
| 5,070,223 A | 12/1991 | Colasante |
| 5,346,458 A | 9/1994 | Affeld |
| 5,350,413 A | 9/1994 | Miller et al. |
| 5,569,156 A | 10/1996 | Mussivand |
| 5,630,836 A | 5/1997 | Prem et al. |
| 5,690,693 A | 11/1997 | Wang et al. |
| 5,702,431 A | 12/1997 | Wang et al. |
| 5,755,748 A | 5/1998 | Borza |
| 5,771,438 A | 6/1998 | Palermo et al. |
| 5,831,248 A | 11/1998 | Hojyo et al. |
| 5,948,006 A | 9/1999 | Mann |
| 6,123,726 A | 9/2000 | Mori et al. |
| 6,149,683 A | 11/2000 | Lancisi et al. |
| 6,212,430 B1 | 4/2001 | Kung |
| 6,296,533 B1 | 10/2001 | Grubbs et al. |
| 6,312,338 B1 | 11/2001 | Sato et al. |
| 6,320,354 B1 | 11/2001 | Sengupta et al. |
| 6,324,431 B1 | 11/2001 | Zarinetchi et al. |
| 6,327,504 B1 | 12/2001 | Dolgin et al. |
| 6,389,318 B1 | 5/2002 | Zarinetchi et al. |
| 6,400,991 B1 | 6/2002 | Kung |
| 6,442,434 B1 | 8/2002 | Zarinetchi et al. |
| 6,451,055 B1 | 9/2002 | Weiss |
| 6,458,164 B1 | 10/2002 | Weiss |
| 6,478,820 B1 | 11/2002 | Weiss |
| 6,553,263 B1 | 4/2003 | Meadows et al. |
| 6,579,315 B1 | 6/2003 | Weiss |
| 6,591,139 B2 | 7/2003 | Loftin et al. |
| 6,605,032 B2 | 8/2003 | Benkowski et al. |
| 6,647,298 B2 | 11/2003 | Abrahamson et al. |
| 6,650,213 B1 | 11/2003 | Sakurai et al. |
| 6,723,039 B2 | 4/2004 | French et al. |
| 6,772,011 B2 | 8/2004 | Dolgin |
| 6,801,807 B2 | 10/2004 | Abrahamson |
| 6,810,289 B1 | 10/2004 | Shaquer |
| 6,850,803 B1 | 2/2005 | Jimenez et al. |
| 6,894,456 B2 | 5/2005 | Tsukamoto et al. |
| 6,895,281 B1 | 5/2005 | Amundson et al. |
| 6,949,065 B2 | 9/2005 | Sporer et al. |
| 6,960,968 B2 | 11/2005 | Odenaal et al. |
| 6,967,621 B1 | 11/2005 | Cadotte, Jr. et al. |
| 6,985,773 B2 | 1/2006 | Von Arx et al. |
| 7,015,769 B2 | 3/2006 | Schulman et al. |
| 7,107,103 B2 | 9/2006 | Schulman et al. |
| 7,126,310 B1 | 10/2006 | Barron |
| 7,225,032 B2 | 5/2007 | Schmeling et al. |
| 7,246,040 B2 | 7/2007 | Borg et al. |
| 7,286,880 B2 | 10/2007 | Olson et al. |
| 7,428,438 B2 | 9/2008 | Parramon et al. |
| 7,471,986 B2 | 12/2008 | Hatlestad |
| 7,496,733 B2 | 2/2009 | Altman et al. |
| 7,505,816 B2 | 3/2009 | Schmeling et al. |
| 7,515,012 B2 | 4/2009 | Schulman et al. |
| 7,522,878 B2 | 4/2009 | Baarman |
| 7,532,901 B1 | 5/2009 | LaFranchise et al. |
| 7,565,187 B1 | 7/2009 | Dynok et al. |
| 7,571,007 B2 | 8/2009 | Erickson et al. |
| 7,587,241 B2 | 9/2009 | Parramon et al. |
| 7,599,743 B2 | 10/2009 | Hassler et al. |
| 7,650,187 B2 | 1/2010 | Gruber et al. |
| 7,650,192 B2 | 1/2010 | Wahlstrand |
| 7,711,433 B2 | 5/2010 | Davis et al. |
| 7,720,546 B2 | 5/2010 | Ginggen et al. |
| 7,741,734 B2 | 6/2010 | Joannopoulos et al. |
| 7,761,164 B2 | 7/2010 | Verhoef et al. |
| 7,774,069 B2 | 8/2010 | Olson et al. |
| 7,782,190 B1 | 8/2010 | Martin et al. |
| 7,805,200 B2 | 9/2010 | Kast et al. |
| 7,812,481 B2 | 10/2010 | Iisaka et al. |
| 7,818,036 B2 | 10/2010 | Lair et al. |
| 7,818,037 B2 | 10/2010 | Lair et al. |
| 7,825,543 B2 | 11/2010 | Karalis et al. |
| 7,830,114 B2 | 11/2010 | Reed |
| 7,865,245 B2 | 1/2011 | Torgerson et al. |
| 7,872,367 B2 | 1/2011 | Recksiek et al. |
| 7,904,170 B2 | 3/2011 | Harding |
| 7,932,696 B2 | 4/2011 | Peterson et al. |
| 7,962,222 B2 | 6/2011 | He et al. |
| RE42,682 E | 9/2011 | Barreras, Sr. et al. |
| 8,076,801 B2 | 12/2011 | Karalis et al. |
| 8,081,925 B2 | 12/2011 | Parramon et al. |
| 8,096,954 B2 | 1/2012 | Stahmann et al. |
| 8,140,168 B2 | 3/2012 | Olson et al. |
| 8,150,529 B2 | 4/2012 | Snell et al. |
| 8,165,694 B2 | 4/2012 | Carbunaru et al. |
| 8,185,212 B2 | 5/2012 | Carbunaru et al. |
| 8,193,766 B2 | 6/2012 | Rondoni et al. |
| 8,203,434 B2 | 6/2012 | Yoshida |
| 8,244,367 B2 | 8/2012 | Wahlstrand et al. |
| 8,247,926 B2 | 8/2012 | Issa et al. |
| 8,258,653 B2 | 9/2012 | Kitamura et al. |
| 8,265,770 B2 | 9/2012 | Toy et al. |
| 8,278,784 B2 | 10/2012 | Cook et al. |
| 8,292,052 B2 | 10/2012 | Bohori et al. |
| 8,299,652 B2 | 10/2012 | Smith et al. |
| 8,301,079 B2 | 10/2012 | Baarman |
| 8,319,473 B2 | 11/2012 | Choi et al. |
| 8,362,742 B2 | 1/2013 | Kallmyer |
| 8,373,310 B2 | 2/2013 | Baarman et al. |
| 8,378,522 B2 | 2/2013 | Cook et al. |
| 8,378,523 B2 | 2/2013 | Cook et al. |
| 8,463,395 B2 | 6/2013 | Forsell |
| 8,489,200 B2 | 7/2013 | Zarinetchi et al. |
| 8,551,163 B2 | 10/2013 | Aber et al. |
| 8,562,508 B2 | 10/2013 | Dague et al. |
| 8,581,793 B2 | 11/2013 | Carr |
| 8,587,154 B2 | 11/2013 | Fells et al. |
| 8,620,447 B2 | 12/2013 | D'Ambrosio et al. |
| 8,628,460 B2 | 1/2014 | Yomtov et al. |
| 8,629,578 B2 | 1/2014 | Kurs et al. |
| 8,668,473 B2 | 3/2014 | Larose et al. |
| 8,694,117 B2 | 4/2014 | Aghassian et al. |
| 8,810,071 B2 | 8/2014 | Sauerlaender et al. |
| 8,884,468 B2 | 11/2014 | Lemmens et al. |
| 8,909,351 B2 | 12/2014 | Dinsmoor et al. |
| 8,971,958 B2 | 3/2015 | Frikart et al. |
| 9,002,468 B2 | 4/2015 | Shea et al. |
| 9,106,083 B2 | 8/2015 | Partovi |
| 9,192,704 B2 | 11/2015 | Yomtov et al. |
| 9,302,093 B2 | 4/2016 | Mashiach |
| 9,515,494 B2 | 12/2016 | Kurs et al. |
| 9,515,495 B2 | 12/2016 | Kurs et al. |
| 9,560,787 B2 | 1/2017 | Kallmyer et al. |
| 2002/0038138 A1 | 3/2002 | Zarinetchi et al. |
| 2002/0087204 A1 | 7/2002 | Kung et al. |

(56) References Cited

U.S. PATENT DOCUMENTS

| | | |
|---|---|---|
| 2002/0093456 A1 | 7/2002 | Sawamura et al. |
| 2003/0171792 A1* | 9/2003 | Zarinetchi ............ A61N 1/3787 607/61 |
| 2004/0138725 A1 | 7/2004 | Forsell |
| 2004/0256146 A1 | 12/2004 | Frericks et al. |
| 2005/0006083 A1 | 1/2005 | Chen et al. |
| 2005/0288743 A1 | 12/2005 | Ahn et al. |
| 2006/0199997 A1 | 9/2006 | Hassler et al. |
| 2006/0271129 A1 | 11/2006 | Tai et al. |
| 2007/0096686 A1 | 5/2007 | Jimenez et al. |
| 2007/0123948 A1 | 5/2007 | Dal Molin |
| 2007/0142696 A1 | 6/2007 | Crosby et al. |
| 2007/0191706 A1 | 8/2007 | Calderon et al. |
| 2008/0009198 A1 | 1/2008 | Marino |
| 2008/0027293 A1 | 1/2008 | Vodermayer et al. |
| 2008/0054638 A1 | 3/2008 | Greene et al. |
| 2008/0100294 A1 | 5/2008 | Rohling et al. |
| 2008/0149736 A1 | 6/2008 | Kim et al. |
| 2008/0167531 A1 | 7/2008 | McDermott |
| 2008/0211320 A1 | 9/2008 | Cook et al. |
| 2009/0018616 A1 | 1/2009 | Quick et al. |
| 2009/0051224 A1 | 2/2009 | Cook et al. |
| 2009/0072628 A1 | 3/2009 | Cook et al. |
| 2009/0079268 A1* | 3/2009 | Cook ..................... H01Q 1/248 307/104 |
| 2009/0081943 A1 | 3/2009 | Dobyns et al. |
| 2009/0174264 A1 | 7/2009 | Onishi et al. |
| 2009/0212736 A1 | 8/2009 | Baarman et al. |
| 2009/0226328 A1 | 9/2009 | Morello |
| 2009/0270679 A1 | 10/2009 | Hoeg et al. |
| 2009/0284220 A1 | 11/2009 | Toncich et al. |
| 2010/0019985 A1 | 1/2010 | Bashyam et al. |
| 2010/0033021 A1 | 2/2010 | Bennett |
| 2010/0035453 A1 | 2/2010 | Tronnes et al. |
| 2010/0045114 A1 | 2/2010 | Sample et al. |
| 2010/0063347 A1 | 3/2010 | Yomtov et al. |
| 2010/0066305 A1 | 3/2010 | Takahashi et al. |
| 2010/0069992 A1 | 3/2010 | Aghassian et al. |
| 2010/0109958 A1 | 5/2010 | Haubrich et al. |
| 2010/0114143 A1 | 5/2010 | Albrecht et al. |
| 2010/0122995 A1 | 5/2010 | Thomas et al. |
| 2010/0171368 A1 | 7/2010 | Schatz et al. |
| 2010/0184371 A1 | 7/2010 | Cook et al. |
| 2010/0194334 A1 | 8/2010 | Kirby et al. |
| 2010/0210233 A1 | 8/2010 | Cook et al. |
| 2010/0211134 A1 | 8/2010 | Forsell |
| 2010/0222848 A1 | 9/2010 | Forsell |
| 2010/0222849 A1 | 9/2010 | Forsell |
| 2010/0225174 A1 | 9/2010 | Jiang |
| 2010/0244576 A1 | 9/2010 | Hillan et al. |
| 2010/0253340 A1 | 10/2010 | Corum et al. |
| 2010/0256708 A1 | 10/2010 | Thornton et al. |
| 2010/0277121 A1 | 11/2010 | Hall et al. |
| 2010/0308939 A1 | 12/2010 | Kurs |
| 2010/0314946 A1 | 12/2010 | Budde et al. |
| 2010/0320843 A1* | 12/2010 | Kitamura ................ H01F 27/34 307/104 |
| 2010/0331919 A1 | 12/2010 | DiGiore et al. |
| 2011/0025132 A1 | 2/2011 | Sato |
| 2011/0043050 A1 | 2/2011 | Yabe et al. |
| 2011/0046699 A1 | 2/2011 | Mazanec et al. |
| 2011/0057607 A1 | 3/2011 | Carobolante |
| 2011/0101790 A1 | 5/2011 | Budgett |
| 2011/0109263 A1 | 5/2011 | Sakoda et al. |
| 2011/0115431 A1 | 5/2011 | Dunworth et al. |
| 2011/0127848 A1 | 6/2011 | Ryu et al. |
| 2011/0148215 A1 | 6/2011 | Marzetta et al. |
| 2011/0178361 A1 | 7/2011 | Yomtov |
| 2011/0181235 A1 | 7/2011 | Walley et al. |
| 2011/0205083 A1 | 8/2011 | Janna et al. |
| 2011/0234155 A1 | 9/2011 | Chen et al. |
| 2011/0241436 A1 | 10/2011 | Furukawa |
| 2011/0245892 A1 | 10/2011 | Kast et al. |
| 2011/0266880 A1 | 11/2011 | Kim et al. |
| 2011/0276110 A1 | 11/2011 | Whitehurst et al. |
| 2011/0278948 A1 | 11/2011 | Forsell |
| 2011/0291489 A1 | 12/2011 | Tsai et al. |
| 2011/0291613 A1 | 12/2011 | Rosik et al. |
| 2011/0295345 A1 | 12/2011 | Wells et al. |
| 2011/0298294 A1 | 12/2011 | Takada et al. |
| 2011/0301667 A1 | 12/2011 | Olson et al. |
| 2011/0313238 A1 | 12/2011 | Reichenbach et al. |
| 2012/0001485 A1 | 1/2012 | Uchida |
| 2012/0032522 A1 | 2/2012 | Schatz et al. |
| 2012/0039102 A1 | 2/2012 | Shinoda |
| 2012/0057322 A1 | 3/2012 | Waffenschmidt |
| 2012/0065458 A1 | 3/2012 | Tol |
| 2012/0080957 A1 | 4/2012 | Cooper et al. |
| 2012/0091951 A1 | 4/2012 | Sohn |
| 2012/0104997 A1 | 5/2012 | Carobolante |
| 2012/0109256 A1 | 5/2012 | Meskins et al. |
| 2012/0119914 A1 | 5/2012 | Uchida |
| 2012/0146575 A1 | 6/2012 | Armstrong et al. |
| 2012/0149229 A1 | 6/2012 | Kearsley et al. |
| 2012/0150259 A1 | 6/2012 | Meskens |
| 2012/0153739 A1 | 6/2012 | Cooper et al. |
| 2012/0153954 A1 | 6/2012 | Ota et al. |
| 2012/0157753 A1 | 6/2012 | D'Ambrosio |
| 2012/0157754 A1 | 6/2012 | D'Ambrosio |
| 2012/0158407 A1 | 6/2012 | Forsell |
| 2012/0161539 A1 | 6/2012 | Kim et al. |
| 2012/0164943 A1 | 6/2012 | Bennett |
| 2012/0169132 A1 | 7/2012 | Choudhary et al. |
| 2012/0169133 A1 | 7/2012 | Lisi et al. |
| 2012/0169137 A1 | 7/2012 | Lisi et al. |
| 2012/0169139 A1 | 7/2012 | Kudo |
| 2012/0169278 A1 | 7/2012 | Choi et al. |
| 2012/0175967 A1 | 7/2012 | Dibben et al. |
| 2012/0235364 A1 | 9/2012 | Wang et al. |
| 2012/0239118 A1 | 9/2012 | Ozawa et al. |
| 2012/0245649 A1 | 9/2012 | Bohori et al. |
| 2012/0245664 A1 | 9/2012 | Smith et al. |
| 2012/0259398 A1 | 10/2012 | Chen et al. |
| 2012/0274148 A1 | 11/2012 | Sung et al. |
| 2012/0306433 A1 | 12/2012 | Kim et al. |
| 2013/0007949 A1 | 1/2013 | Kurs et al. |
| 2013/0060103 A1 | 3/2013 | Bergida et al. |
| 2013/0119773 A1 | 5/2013 | Davis |
| 2013/0127253 A1 | 5/2013 | Stark et al. |
| 2013/0149960 A1 | 6/2013 | Dec et al. |
| 2013/0159956 A1 | 6/2013 | Verghese et al. |
| 2013/0190551 A1 | 7/2013 | Callaway et al. |
| 2013/0197607 A1 | 8/2013 | Wilder et al. |
| 2013/0214731 A1 | 8/2013 | Dinsmoor et al. |
| 2013/0241306 A1 | 9/2013 | Aber et al. |
| 2013/0241468 A1 | 9/2013 | Moshfeghi |
| 2013/0271088 A1 | 10/2013 | Hwang et al. |
| 2013/0289334 A1 | 10/2013 | Badstibner et al. |
| 2013/0310630 A1 | 11/2013 | Smith et al. |
| 2013/0320773 A1 | 12/2013 | Schatz et al. |
| 2013/0331638 A1 | 12/2013 | Cameron et al. |
| 2014/0005466 A1 | 1/2014 | Crosby et al. |
| 2014/0011447 A1 | 1/2014 | Konanur et al. |
| 2014/0028110 A1 | 1/2014 | Petersen et al. |
| 2014/0028111 A1 | 1/2014 | Hansen et al. |
| 2014/0031606 A1 | 1/2014 | Hansen et al. |
| 2014/0152252 A1 | 6/2014 | Wood |
| 2014/0163644 A1 | 6/2014 | Scott et al. |
| 2014/0265620 A1 | 9/2014 | Hoarau et al. |
| 2014/0265621 A1 | 9/2014 | Wong et al. |
| 2014/0275727 A1 | 9/2014 | Bonde et al. |
| 2015/0123654 A1 | 5/2015 | Gagnon et al. |
| 2015/0180241 A1 | 6/2015 | Petersen et al. |
| 2015/0207330 A1 | 7/2015 | Petersen |
| 2015/0207331 A1 | 7/2015 | Petersen |
| 2015/0222127 A1 | 8/2015 | Hansen et al. |
| 2015/0222139 A1 | 8/2015 | Petersen et al. |
| 2015/0229289 A1 | 8/2015 | Suzuki |
| 2015/0290373 A1 | 10/2015 | Rudser et al. |
| 2016/0135684 A1 | 5/2016 | Kappel et al. |
| 2016/0218432 A1 | 7/2016 | Pope et al. |
| 2016/0250484 A1 | 9/2016 | Nguyen et al. |

(56) References Cited

U.S. PATENT DOCUMENTS

| | | |
|---|---|---|
| 2016/0254703 A1 | 9/2016 | Hansen |
| 2016/0254704 A1 | 9/2016 | Hansen et al. |

FOREIGN PATENT DOCUMENTS

| | | |
|---|---|---|
| EP | 0589608 A2 | 3/1994 |
| EP | 1513241 A1 | 3/2005 |
| EP | 2267864 A2 | 12/2010 |
| GB | 2477034 A | 7/2011 |
| JP | H03109063 A | 5/1991 |
| JP | H11506646 A | 6/1999 |
| JP | 2013094456 A | 5/2013 |
| JP | 2013161640 A | 8/2013 |
| JP | 2014160611 A | 9/2014 |
| KR | 1020020089605 A | 11/2002 |
| KR | 1020120007296 A | 1/2012 |
| KR | 1020120077448 A | 7/2012 |
| WO | 0001442 A2 | 1/2000 |
| WO | 0074747 A1 | 12/2000 |
| WO | 0137926 A1 | 5/2001 |
| WO | 2005106901 A2 | 11/2005 |
| WO | 2007053881 A1 | 5/2007 |
| WO | 2008066941 A2 | 6/2008 |
| WO | 2009018271 A1 | 2/2009 |
| WO | 2009021220 A1 | 2/2009 |
| WO | 2009023905 A1 | 2/2009 |
| WO | 2009042977 A1 | 4/2009 |
| WO | 2010030378 A1 | 3/2010 |
| WO | 2010089354 A2 | 8/2010 |
| WO | 2011081626 A1 | 7/2011 |
| WO | 2011113934 A1 | 9/2011 |
| WO | 2012002063 A1 | 1/2012 |
| WO | 2012056365 A2 | 5/2012 |
| WO | 2012087807 A2 | 6/2012 |
| WO | 2012087811 A2 | 6/2012 |
| WO | 2012087816 A2 | 6/2012 |
| WO | 2012087819 A2 | 6/2012 |
| WO | 2012099965 A2 | 7/2012 |
| WO | 2012141752 A2 | 10/2012 |
| WO | 2013110602 A1 | 8/2013 |
| WO | 2013138451 A1 | 9/2013 |
| WO | 2014039673 A1 | 3/2014 |

OTHER PUBLICATIONS

Chargepoint, Inc.; -chargepoin+®; product brochure; 4 pgs.; © 2014; retrieved Mar. 12, 2014 from the internet: http://www.chargepoint.com/network/.

Dixon, Jr.; Eddy current losses in transformer windings and circuit wiring; Unitrode Corp. Seminar Manual (SEM600); Watertown, MA; 12 pgs.; 1988 (year of pub. sufficiently earlier than effective US filing date and any foreign priority date).

Evatran; PluglessTM Level 2 EV Charging System (3.3kW); product brochure; 7 pgs.; retrieved Mar. 12, 2014 from the internet: http://www.pluglesspower.com/tech-specs/.

Ferret, B.; Electric vehicles get big boost!; Renewable Energy World; 3 pgs.; Jul. 30, 2012; retrieved Jul. 30, 2012 from the internet: http://www.renewableenergyworld.com/rea/blog/post/2012/07/.

Motavalli, Jim; WiTricity Takes Its Car-Charging Technology Out for a Road Test; New York Times; 3 pgs.; Jul. 25, 2012; retrieved Mar. 12, 2014 from the internet: http://wheels.blogs.nytimes.com/2012/07/25/witricity-takes-its-car-charging-technology-out-for-a-road-test/.

Notification of Transmittal of the International Search Report and the Written Opinion of the International Searching Authority for PCT Application No. PCT/US2015/051474, dated Dec. 30, 2015.

Development and Implementation of RFID Technology, Ed. Cristina Turcu, Feb. 2009, pp. 28-30, 93-97.

Merli, Francesco, et al., "Design, Realization and Measurements of a Miniature Antenna for Implantable Wireless Communication Systems", IEEE Transaction on Antennas and Propagation, vol. 59, No. 10, Oct. 2011, pp. 3544-3555.

Merli, Francesco, et al.,"The Effect of Insulating Layers on the Performance of Implanted Antennas", IEEE Transaction on Antennas and Propagation, vol. 59, No. 1, Jan. 2011, pp. 21-31.

Abadia, Javier, et al., 3D-Spiral Small Antenna Design and Realization for Biomdical Telemetry in the MICS Band. Radioengineering, vol. 18, No. 4, Dec. 2009, pp. 359-367.

\* cited by examiner $$k \approx \frac{A_2}{A_1}$$

$$k \approx \frac{A_2}{A_1}\cos\theta$$

RESONANT POWER TRANSMISSION COILS AND SYSTEMS

CROSS-REFERENCE TO RELATED APPLICATIONS

This application is a continuation of U.S. application Ser. No. 14/414,842, filed on Jan. 14, 2015, titled "Resonant Power Transmission Coils and Systems", which claims the benefit of U.S. Provisional Patent Application No. 61/676,718, filed on Jul. 27, 2012, titled "Resonant Power Transmission Coils and Systems", both of which are hereby incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure relates generally to methods and apparatus for transmitting and receiving power wirelessly, and in various respects, mechanical circulatory support.

BACKGROUND

Powered devices need to have a mechanism to supply power to the operative parts. Typically systems use a physical power cable to transfer energy over a distance. There has been a continuing need for systems that can transmit power efficiently over a distance without physical structures bridging the physical gap.

Systems and methods that supply power without electrical wiring are sometimes referred to as wireless energy transmission (WET). Wireless energy transmission greatly expands the types of applications for electrically powered devices. One such example is the field of implantable medical devices. Implantable medical devices typically require an internal power source able to supply adequate power for the reasonable lifetime of the device or an electrical cable that traverses the skin. Typically an internal power source (e.g. battery) is feasibly for only low power devices like sensors. Likewise, a transcutaneous power cable significantly affects quality of life (QoL), infection risk, and product life, among many drawbacks.

More recently there has been an emphasis on systems that supply power to an implanted device without using transcutaneous wiring. This is sometimes referred to as a Transcutaneous Energy Transfer System (TETS). Frequently energy transfer is accomplished using two magnetically coupled coils set up like a transformer so power is transferred magnetically across the skin. Conventional systems are relatively sensitive to variations in position and alignment of the coils. In order to provide constant and adequate power, the two coils need to be physically close together and well aligned.

Other solutions have focused on making one or both of the coils larger so the magnetic flux field is larger. This provides greater freedom of movement of the coils while ensuring efficient power transfer. This approach has several drawbacks. Because the components are implanted in the body, a larger receiving coil makes surgical placement more difficult and limits the implantation options. In cases where the transmitter is large relative to the receiver, it is likely the transmitter will be set up to generate a large field, then the receiver will have to adjust to keep its output in a reasonable range, and optimize for efficiency.

Enlarging the transmission coil has several drawbacks. The transmitter is effectively set up to blast out the maximum field, which necessitates careful power management on the receiver side. The transmitter is set up to operate passively, and the receiver is doing most of the control. Thus, this system can be complex to implement, especially in sensitive applications like implantable medical devices. A larger transmission coil decreases quality of life (QoL) because the patient must carry a larger, heavier coil. Moreover, larger coils inherently lead to greater complexity. The system inherently carries the risk of providing too much power to the internal load and/or battery. Higher power transfer can also lead to excessive heating, which risk damaging the internal organs and tissue.

In cases where the transmitter is smaller, such as a mobile wearable coil, transmitter efficiency is important. The system is highly sensitive to receiver coil position and orientation and may not provide adequate power transfer in all cases.

Another drawback with conventional wireless power transmission systems is high susceptibility to interference. Even minor changes to the field from external factors can significantly affect the transmitter and receiver. For example, if a metallic object is introduced into the system, it will affect the magnetic flux and in turn the system will not operate efficiently.

SUMMARY OF THE DISCLOSURE

In summary, one aspect of the present invention is directed to an implantable receiver for wirelessly receiving energy from a transmitter, including a housing enclosing volume including a receiving coil and components susceptible to interference by magnetic flux; a covering around at least a portion of the housing; at least one wire wrapped around the housing to form a plurality of turns; wherein the covering is formed of a ferrite material configured to both magnetically shield a respective portion of the internal volume and redirect incoming magnetic flux.

In various embodiments, the receiver includes coil circuitry including at least two coils; and receiver circuitry configured to transmit power excited in the receiver coil in response to exposure to a field to a load. In various embodiments, the load is an implantable medical device including an operative component. The operative component may be a circulatory support device. The operative component may be a blood pump for supporting and/or replacing the function of the heart. The operative component may be a left ventricular assist device, right ventricular assist device, bi-ventricular assist device, and/or total artificial heart. All or part of the operative component may be external to the body.

In various embodiments, the covering comprises a plurality of tiles. In various embodiments, the covering covers the entire housing periphery.

Various aspects of the invention are directed to a system including a receiver, a transmitter for generating a magnetic field to the receiver, and an implantable mechanical circulatory support (MCS) device. In various embodiments, the MCS device is configured to be powered by energy from the receiver. In various embodiments, the system further includes an implantable battery. In various embodiments, the MCS device is configured to be powered by one of the receiver, the battery, or a combination thereof. In various embodiments, the system further includes an implantable controller.

Another aspect of the present invention is directed to a method of using the system, and in particular the receiver. In various respects the invention is directed to wirelessly transmitting energy comprising energizing a transmitter to generate a magnetic field, and positioning the receiver in the magnetic field to induce a voltage in the receiver coil. In various embodiments, the method includes positioning the receiver in a mammalian body. In various embodiments, the method includes positioning the receiver in a patient suffering from heart failure, cardiogenic shock, or undergoing high risk surgery (e.g. percutaneous coronary intervention). In various embodiments, the method includes positioning the receiver in the chest cavity of a human.

The receiver and wireless energy transmission system of the various inventions have other features and advantages which will be apparent from or are set forth in more detail in the accompanying drawings, which are incorporated in and form a part of this specification, and the following Detailed Description of the Invention, which together serve to explain the principles of the present invention.

An implantable receiver configured to receive wireless energy is provided, comprising a housing including internal components susceptible to interference by magnetic flux, a covering disposed on at least a portion of the housing, the covering being formed of a ferrite material configured to both magnetically shield a respective portion of components in the housing and redirect incoming magnetic flux from an external transmitter, at least two wires wrapped around the housing to form a receiver coil.

In some embodiments, the internal components of the receiver comprise receiver circuitry configured to transmit power excited in the receiver coil in response to the incoming magnetic flux to a load connected to the implantable receiver.

In other embodiments, the load is an implantable medical device including an operative component.

In some embodiments, the operative component is a circulatory support device.

In another embodiment, the operative component is a blood pump.

In some embodiments, the covering comprises a plurality of tiles.

In another embodiment, the covering covers the entire housing periphery.

In some embodiments, the covering is configured to redirect incoming magnetic flux from the external transmitter towards the receiver coil to improve power transfer efficiency.

A method of improving efficiency in a wireless power transfer system is also provided, comprising the steps of generating magnetic flux with an external transmitter positioned near a patient towards a receiver implanted in the patient, and directing the magnetic flux towards a receiver coil of the receiver with a ferrite covering that surrounds at least a portion of the receiver.

In one embodiment, the covering comprises a plurality of ferrite tiles.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

In FIG. 3B, half the flux from one coil is in one direction, and the other half is in the other direction.

DETAILED DESCRIPTION

Figure 1:
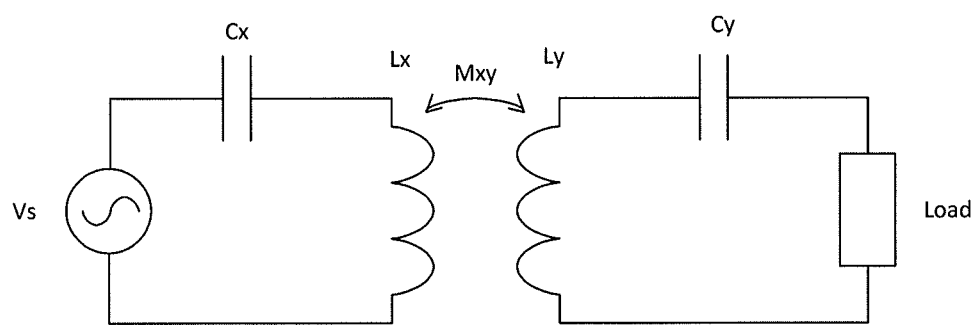
FIG. 1 is a schematic of a simplified circuit for wireless energy transmission system in accordance with various aspects of the invention.

In the description that follows, like components have been given the same reference numerals, regardless of whether they are shown in different embodiments. To illustrate an embodiment(s) of the present disclosure in a clear and concise manner, the drawings may not necessarily be to scale and certain features may be shown in somewhat schematic form. Features that are described and/or illustrated with respect to one embodiment may be used in the same way or in a similar way in one or more other embodiments and/or in combination with or instead of the features of the other embodiments.

Various aspects of the invention are similar to those described in International Patent Pub. No. WO2012045050; U.S. Pat. Nos. 8,140,168; 7,865,245; 7,774,069; 7,711,433; 7,650,187; 7,571,007; 7,741,734; 7,825,543; 6,591,139; 6,553,263; and 5,350,413; and U.S. Pub. Nos. 2010/0308939; 2008/027293; and 2010/0102639, the entire contents of which patents and applications are incorporated herein for all purposes.

Wireless Power Transmission System

Power may be transmitted wirelessly by magnetic induction. In various embodiments, the transmitter and receiver are closely coupled.

In some cases "closely coupled" or "close coupling" refers to a system that requires the coils to be very near each other in order to operate. In some cases "loosely coupled" or "loose coupling" refers to a system configured to operate when the coils have a significant spatial and/or axial separation, and in some cases up to distance equal to or less than the diameter of the larger of the coils. In some cases, "loosely coupled" or "loose coupling" refers a system that is relatively insensitive to changes in physical separation and/or orientation of the receiver and transmitter.

In various embodiments, the transmitter and receiver are non-resonant coils. For example, a change in current in one coil induces a changing magnetic field. The second coil within the magnetic field picks up the magnetic flux, which in turn induces a current in the second coil. An example of a closely coupled system with non-resonant coils is described in International Pub. No. WO2000/074747, incorporated herein for all purposes by reference. A conventional transformer is another example of a closely coupled, non-resonant system. In various embodiments, the transmitter and receiver are resonant coils. For example, one or both of the coils is connected to a tuning capacitor or other means for controlling the frequency in the respective coil. An example of closely coupled system with resonant coils is described in International Pub. Nos. WO2001/037926; WO2012/087807; WO2012/087811; WO2012/087816; WO2012/087819; WO2010/030378; and WO2012/056365, and U.S. Pub. No. 2003/0171792, incorporated herein for all purposes by reference.

In various embodiments, the transmitter and receiver are loosely coupled. For example, the transmitter can resonate to propagate magnetic flux that is picked up by the receiver at relatively great distances. In some cases energy can be transmitted over several meters. In a loosely coupled system power transfer may not necessarily depend on a critical distance. Rather, the system may be able to accommodate changes to the coupling coefficient between the transmitter and receiver. An example of a loosely coupled system is described in International Pub. No. WO2012/045050, incorporated herein for all purposes by reference.

Power may be transmitted wirelessly by radiating energy. In various embodiments, the system comprises antennas. The antennas may be resonant or non-resonant. For example, non-resonant antennas may radiate electromagnetic waves to create a field. The field can be near field or far field. The field can be directional. Generally far field has greater range but a lower power transfer rate. An example of such a system for radiating energy with resonators is described in International Pub. No. WO2010/089354, incorporated herein for all purposes by reference. An example of such a non-resonant system is described in International Pub. No. WO2009/018271, incorporated herein for all purposes by reference. Instead of antenna, the system may comprise a high energy light source such as a laser. The system can be configured so photons carry electromagnetic energy in a spatially restricted, direct, coherent path from a transmission point to a receiving point. An example of such a system is described in International Pub. No. WO2010/089354, incorporated herein for all purposes by reference.

Power may also be transmitted by taking advantage of the material or medium through which the energy passes. For example, volume conduction involves transmitting electrical energy through tissue between a transmitting point and a receiving point. An example of such a system is described in International Pub. No. WO2008/066941, incorporated herein for all purposes by reference.

Power may also be transferred using a capacitor charging technique. The system can be resonant or non-resonant. Exemplars of capacitor charging for wireless energy transfer are described in International Pub. No. WO2012/056365, incorporated herein for all purposes by reference.

The system in accordance with various aspects of the invention will now be described in connection with a system for wireless energy transfer by magnetic induction. The exemplary system utilizes resonant power transfer. The system works by transmitting power between the two inductively coupled coils. In contrast to a transformer, however, the exemplary coils are not coupled together closely. A transformer generally requires the coils to be aligned and positioned directly adjacent each other. The exemplary system accommodates looser coupling of the coils.

While described in terms of one receiver coil and one transmitter coil, one will appreciate from the description herein that the system may use two or more receiver coils and two or more transmitter coils. For example, the transmitter may be configured with two coils—a first coil to resonate flux and a second coil to excite the first coil. One will further appreciate from the description herein that usage of "resonator" and "coil" may be used somewhat interchangeably. In various respects, "resonator" refers to a coil and a capacitor connected together.

In accordance with various embodiments of this disclosure, the system comprises one or more transmitters configured to transmit power wirelessly to one or more receivers. In various embodiments, the system includes a transmitter and more than one receiver in a multiplexed arrangement. A frequency generator may be electrically coupled to the transmitter to drive the transmitter to transmit power at a particular frequency or range of frequencies. The frequency generator can include a voltage controlled oscillator and one or more switchable arrays of capacitors, a voltage controlled oscillator and one or more varactors, a phase-locked-loop, a direct digital synthesizer, or combinations thereof. The transmitter can be configured to transmit power at multiple frequencies simultaneously. The frequency generator can include two or more phase-locked-loops electrically coupled to a common reference oscillator, two or more independent voltage controlled oscillators, or combinations thereof. The transmitter can be arranged to simultaneously delivery power to multiple receivers at a common frequency.

In various embodiments, the transmitter is configured to transmit a low power signal at a particular frequency. The transmitter may transmit the low power signal for a particular time and/or interval. In various embodiments, the transmitter is configured to transmit a high power signal wirelessly at a particular frequency. The transmitter may transmit the high power signal for a particular time and/or interval.

In various embodiments, the receiver includes a frequency selection mechanism electrically coupled to the receiver coil and arranged to allow the resonator to change a frequency or a range of frequencies that the receiver can receive. The frequency selection mechanism can include a switchable array of discrete capacitors, a variable capacitance, one or more inductors electrically coupled to the receiving antenna, additional turns of a coil of the receiving antenna, or combinations thereof.

In general, most of the flux from the transmitter coil does not reach the receiver coil. The amount of flux generated by the transmitter coil that reaches the receiver coil is described by "k" and referred to as the "coupling coefficient."

In various embodiments, the system is configured to maintain a value of k in the range of between about 0.2 to about 0.01. In various embodiments, the system is configured to maintain a value of k of at least 0.01, at least 0.02, at least 0.03, at least 0.04, or at least 0.05.

In various embodiments, the coils are physically separated. In various embodiments, the separation is greater than a thickness of the receiver coil. In various embodiments, the separation distance is equal to or less than the diameter of the larger of the receiver and transmitter coil.

Because most of the flux does not reach the receiver, the transmitter coil must generate a much larger field than what is coupled to the receiver. In various embodiments, this is accomplished by configuring the transmitter with a large number of amp-turns in the coil.

Since only the flux coupled to the receiver gets coupled to a real load, most of the energy in the field is reactive. The current in the coil can be sustained with a capacitor connected to the coil to create a resonator. The power source thus only needs to supply the energy absorbed by the receiver. The resonant capacitor maintains the excess flux that is not coupled to the receiver.

In various embodiments, the impedance of the receiver is matched to the transmitter. This allows efficient transfer of energy out of the receiver. In this case the receiver coil may not need to have a resonant capacitor.

Turning now to FIG. 1, a simplified circuit for wireless energy transmission is shown. The exemplary system shows a series connection, but the system can be connected as either series or parallel on either the transmitter or receiver side.

The exemplary transmitter includes a coil Lx connected to a power source Vs by a capacitor Cx. The exemplary receiver includes a coil Ly connected to a load by a capacitor Cy. Capacitor Cx may be configured to make Lx resonate at a desired frequency. Capacitance Cx of the transmitter coil may be defined by its geometry. Inductors Lx and Ly are connected by coupling coefficient k. Mxy is the mutual inductance between the two coils. The mutual inductance, Mxy, is related to coupling coefficient, k.

$$Mxy = k\sqrt{Lx \cdot Ly}$$

In the exemplary system the power source Vs is in series with the transmitter coil Lx so it may have to carry all the reactive current. This puts a larger burden on the current rating of the power source and any resistance in the source will add to losses.

The exemplary system includes a receiver configured to receive energy wirelessly transmitted by the transmitter. The exemplary receiver is connected to a load. The receiver and load may be connected electrically with a controllable switch.

In various embodiments, the receiver includes a circuit element configured to be connected or disconnected from the receiver coil by an electronically controllable switch. The electrical coupling can include both a serial and parallel arrangement. The circuit element can include a resistor, capacitor, inductor, lengths of an antenna structure, or combinations thereof. The system can be configured such that power is transmitted by the transmitter and can be received by the receiver in predetermined time increments.

In various embodiments, the transmitter coil and/or the receiver coil is a substantially two-dimensional structure. In various embodiments, the transmitter coil may be coupled to a transmitter impedance-matching structure. Similarly, the receiver coil may be coupled to a receiver impedance-matching structure. Examples of suitable impedance-matching structures include, but are not limited to, a coil, a loop, a transformer, and/or any impedance-matching network. An impedance-matching network may include inductors or capacitors configured to connect a signal source to the resonator structure.

In various embodiments, the transmitter is controlled by a controller (not shown) and driving circuit. The controller and/or driving circuit may include a directional coupler, a signal generator, and/or an amplifier. The controller may be configured to adjust the transmitter frequency or amplifier gain to compensate for changes to the coupling between the receiver and transmitter.

In various embodiments, the transmitter coil is connected to an impedance-matched coil loop. The loop is connected to a power source and is configured to excite the transmitter coil. The first coil loop may have finite output impedance. A signal generator output may be amplified and fed to the transmitter coil. In use power is transferred magnetically between the first coil loop and the main transmitter coil, which in turns transmits flux to the receiver. Energy received by the receiver coil is delivered by Ohmic connection to the load.

One of the challenges to a practical circuit is how to get energy in and out of the resonators. Simply putting the power source and load in series or parallel with the resonators is difficult because of the voltage and current required. In various embodiments, the system is configured to achieve an approximate energy balance by analyzing the system characteristics, estimating voltages and currents involved, and controlling circuit elements to deliver the power needed by the receiver.

In an exemplary embodiment, the system load power, $P_L$, is assumed to be 15 Watts and the operating frequency of the system, f, is 250 kHz. Then, for each cycle the load removes a certain amount of energy from the resonance:

$$e_L = \frac{P_L}{f} = 60 \text{ μJ Energy the load removes from one cycle}$$

$$e_L = \frac{P_L}{f} = 60 \text{ μJ Energy the load removes in one cycle}$$

It has been found that the energy in the receiver resonance is typically several times larger than the energy removed by the load for operative, implantable medical devices. In various embodiments, the system assumes a ratio 7:1 for energy at the receiver versus the load removed. Under this assumption, the instantaneous energy in the exemplary receiver resonance is 420 μJ.

The exemplary circuit was analyzed and the self inductance of the receiver coil was found to be 60 uH. From the energy and the inductance, the voltage and current in the resonator could be calculated.

$$e_y = \frac{1}{2}Li^2$$

$$i_y = \sqrt{\frac{2e_y}{L}} = 3.74 \text{ A peak}$$

$$v_y = \omega L_y i_y = 352 \text{ V peak}$$

The voltage and current can be traded off against each other. The inductor may couple the same amount of flux regardless of the number of turns. The Amp-turns of the coil needs to stay the same in this example, so more turns means the current is reduced. The coil voltage, however, will need to increase. Likewise, the voltage can be reduced at the expense of a higher current. The transmitter coil needs to have much more flux. The transmitter flux is related to the receiver flux by the coupling coefficient. Accordingly, the energy in the field from the transmitter coil is scaled by k.

$$e_x = \frac{e_y}{k}$$

Given that k is 0.05:

$$e_x = \frac{420\ \mu J}{0.05} = 8.4\ mJ$$

For the same circuit the self inductance of the transmitter coil was 146 uH as mentioned above. This results in:

$$i_x = \sqrt{\frac{2e_x}{L}} = 10.7\ A\ peak$$

$$v_x = \omega L_x i_x = 2460\ V\ peak$$

One can appreciate from this example, the competing factors and how to balance voltage, current, and inductance to suit the circumstance and achieve the desired outcome. Like the receiver, the voltage and current can be traded off against each other. In this example, the voltages and currents in the system are relatively high. One can adjust the tuning to lower the voltage and/or current at the receiver if the load is lower.

Estimation of Coupling Coefficient and Mutual Inductance

As explained above, the coupling coefficient, k, may be useful for a number of reasons. In one example, the coupling coefficient can be used to understand the arrangement of the coils relative to each other so tuning adjustments can be made to ensure adequate performance. If the receiver coil moves away from the transmitter coil, the mutual inductance will decrease, and ceteris paribus, less power will be transferred. In various embodiments, the system is configured to make tuning adjustments to compensate for the drop in coupling efficiency.

The exemplary system described above often has imperfect information. For various reasons as would be understood by one of skill in the art, the system does not collect data for all parameters. Moreover, because of the physical gap between coils and without an external means of communications between the two resonators, the transmitter may have information that the receiver does not have and vice versa. These limitations make it difficult to directly measure and derive the coupling coefficient, k, in real time.

Described below are several principles for estimating the coupling coefficient, k, for two coils of a given geometry. The approaches may make use of techniques such as Biot-Savart calculations or finite element methods. Certain assumptions and generalizations, based on how the coils interact in specific orientations, are made for the sake of simplicity of understanding. From an electric circuit point of view, all the physical geometry permutations can generally lead to the coupling coefficient.

Figure 2:
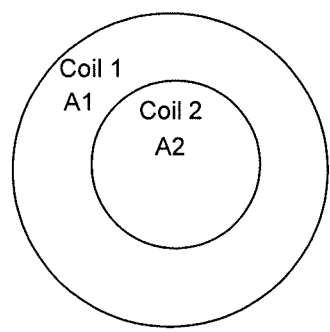
FIG. 2 is a simplified schematic illustrating the relationship between the transmitter and receiver coil sizes and coupling coefficient.

If two coils are arranged so they are in the same plane, with one coil circumscribing the other, then the coupling coefficient can be estimated to be roughly proportional to the ratio of the area of the two coils. This assumes the flux generated by coil 1 is roughly uniform over the area it encloses as shown in FIG. 2.

Figure 3A:
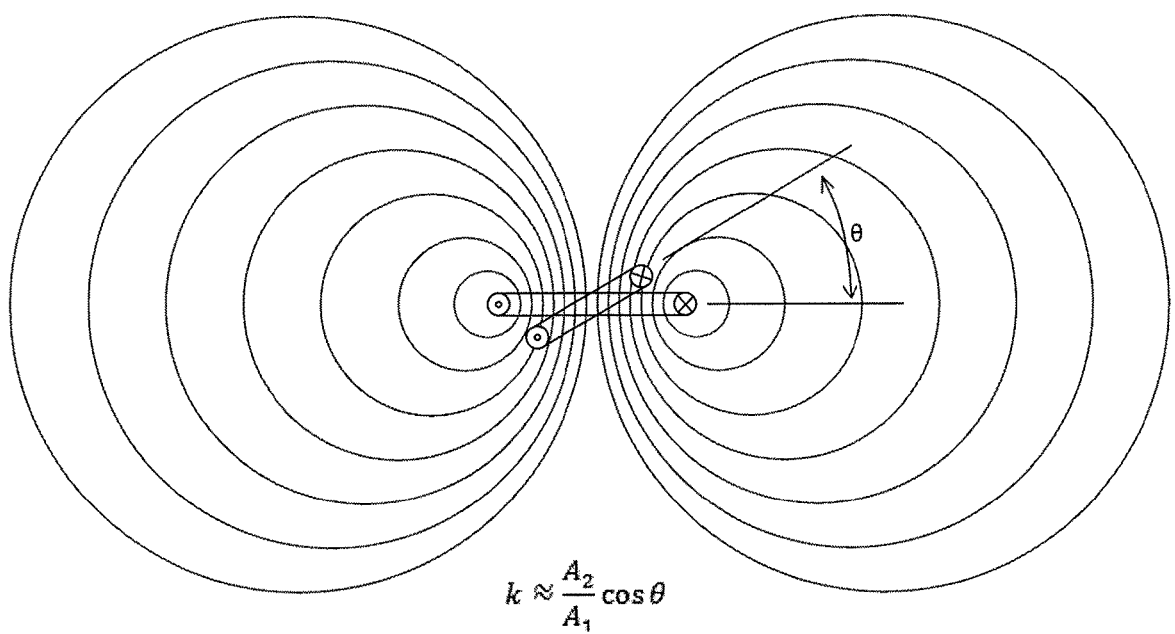
FIG. 3A is a schematic of a transmitter and receiver in operation, the receiver being at an angle theta relative to the transmitter.

If the coils are out of alignment such that the coils are at a relative angle, the coupling coefficient will decrease. The amount of the decrease is estimated to be about equal to the cosine of the angle as shown in FIG. 3A. If the coils are orthogonal to each other such that theta ($\theta$) is 90 degrees, the flux will not be received by the receiver and the coupling coefficient will be zero.

Figure 3B:
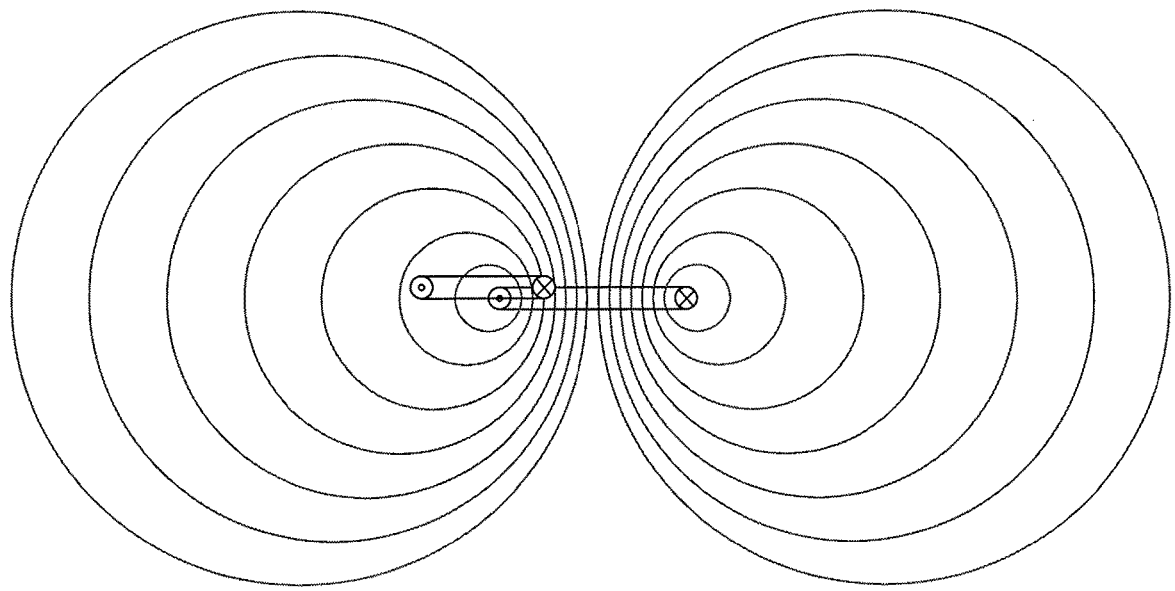
FIG. 3B is a schematic of the transmitter and receiver of FIG. 3A, the receiver being aligned with the transmitter by translated in an axial position so the receiver and transmitter are offset.

If the coils are arranged such that half the flux from one coil is in one direction and the other half is in the other direction, the flux cancels out and the coupling coefficient is zero, as shown in FIG. 3B.

A final principle relies on symmetry of the coils. The coupling coefficient and mutual inductance from one coil to the other is assumed to be the same regardless of which coil is being energized.

$$M_{xy} = M_{yx}$$

Wireless Power Transmission System

For reasons that will be apparent to one of skill from the description herein, even minor influences on the system from external factors can lead to significant changes in the system operation. For example, the introduction of metal to the field can significantly affect the coupling coefficient and mutual inductance.

One way to ensure the system operates effectively is to design the system without consideration of environmental factors and utilize magnetic shielding to isolate the system from external influences. For example, the computer field makes ample use of magnetic shielding to isolate sensitive components within the system.

In one embodiment, the transmitter transmits energy across a specified volume in which the receiver is positioned. The receiver typically includes components that can be negatively affected by the transmitter flux. In various embodiments, the system includes magnetic shielding to isolate the electronic components associated with the receiver coil from interference by the transmitter.

Figure 4:
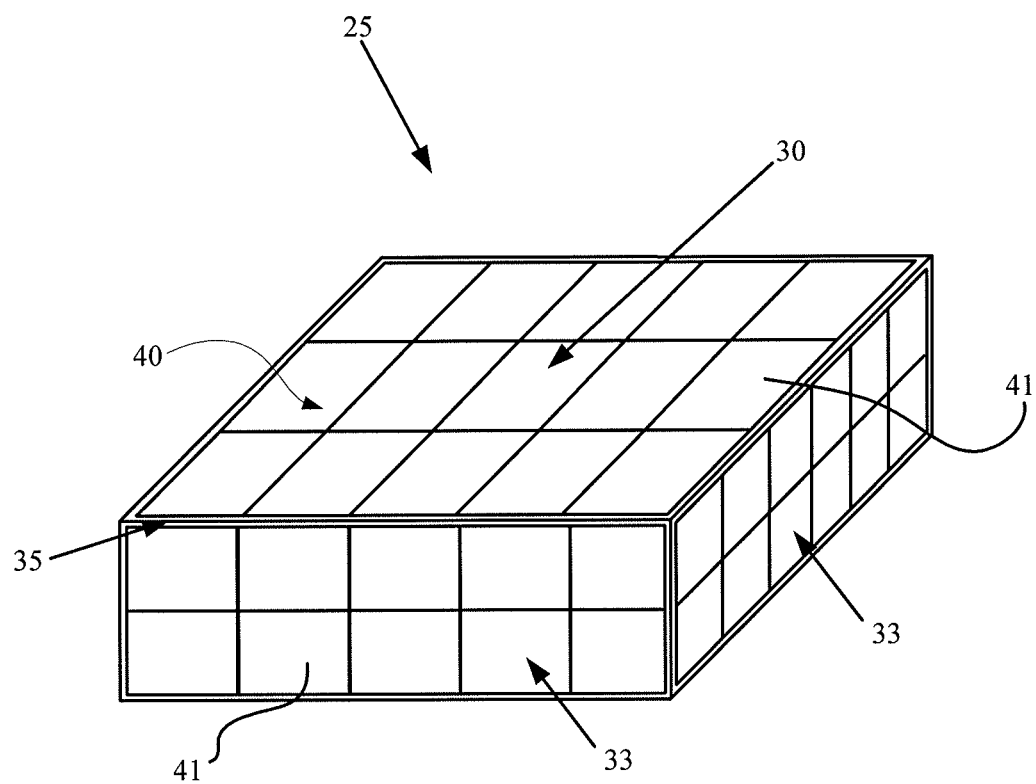
FIG. 4 is a perspective view of a receiver housing in accordance with various aspects of the invention.
Figure 5:
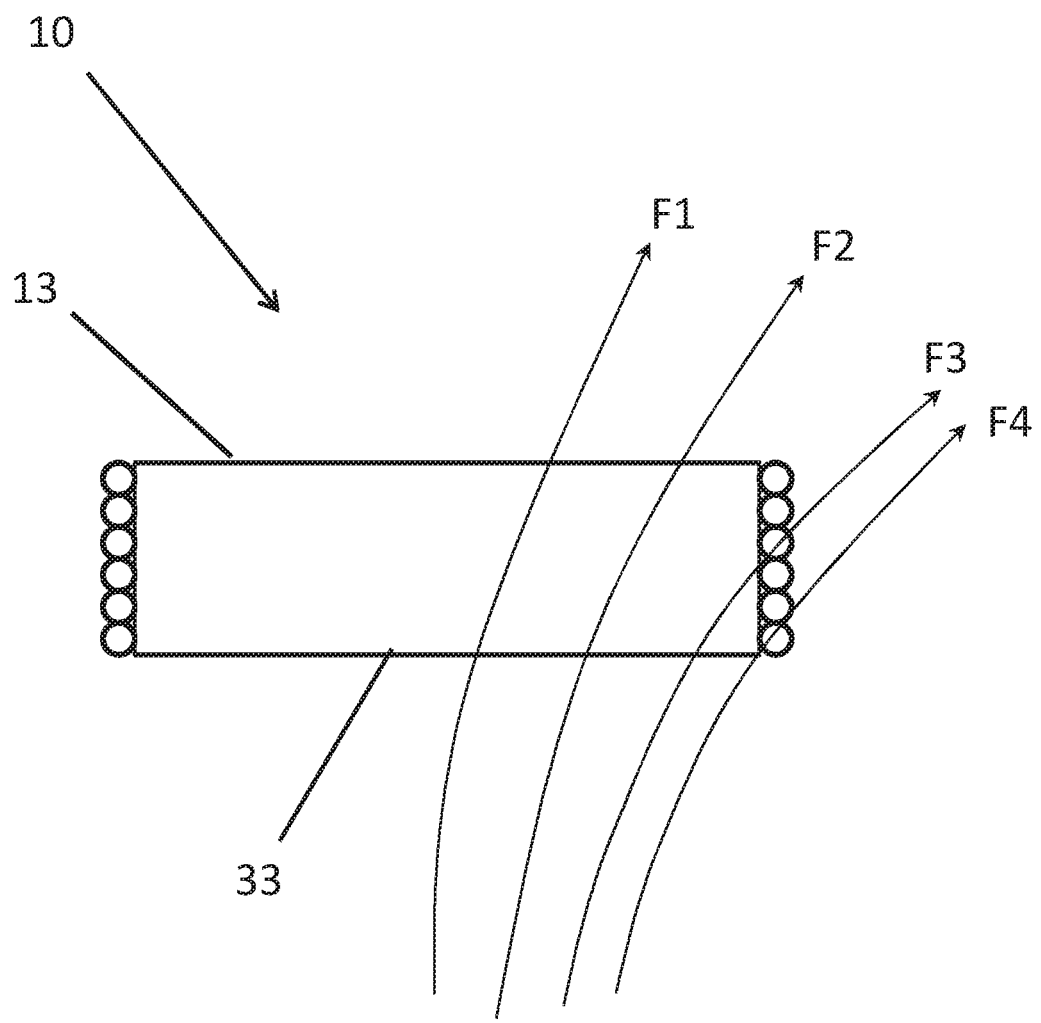
FIG. 5 is a cross-sectional, schematic view of an exemplary receiver positioned in a magnetic field.
Figure 6:
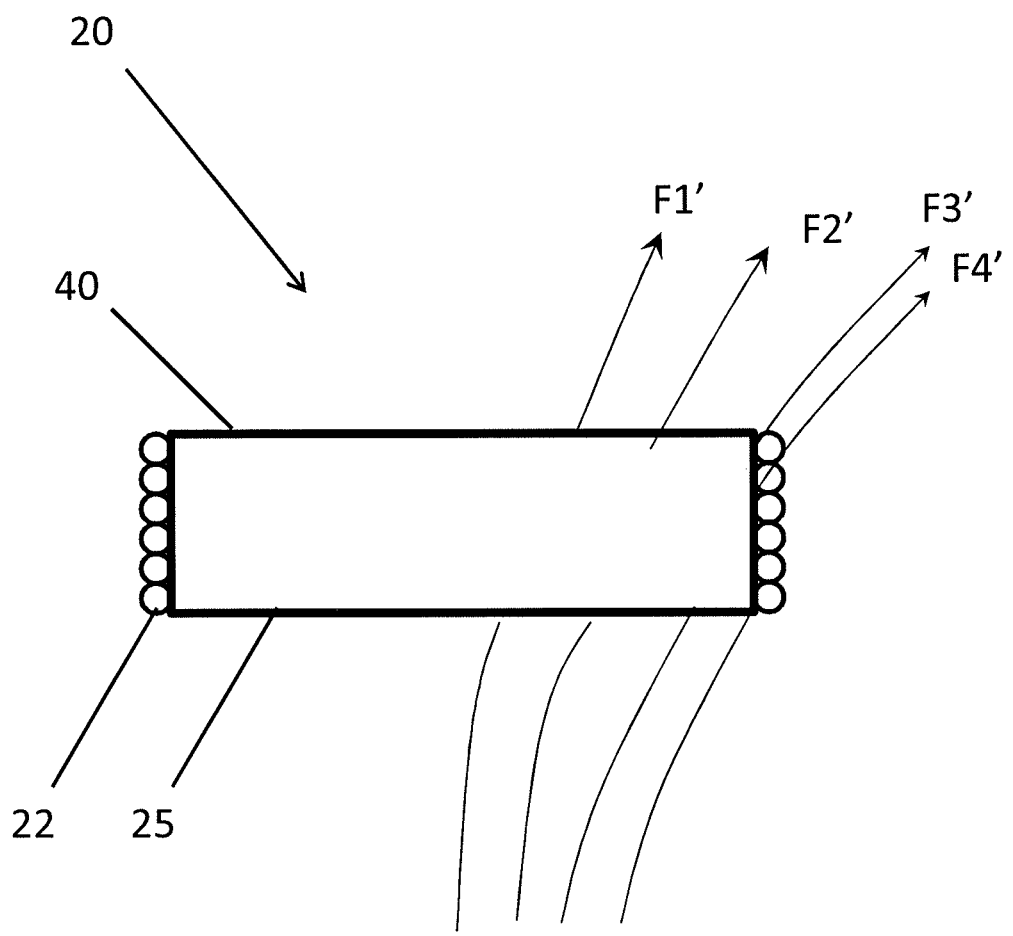
FIG. 6 is a cross-sectional, schematic view of an exemplary receiver positioned in a magnetic field, the receiver including a ferrite covering in accordance with various aspects of the invention.

With reference generally to FIGS. 4-6, one embodiment includes a structure for two purposes—magnetically shielding components within the receiver enclosure from the transmitter and adjusting the path of the flux lines otherwise passing through the enclosure. The system can provide several advantages over existing systems. The use of a single structure for magnetic shielding and focusing and/or redirecting flux provides a simple and effective solution. The system eliminates the need for two or more structures. This is critical for implantable devices where the form factor, and reducing both the size and weight of the implant, is of utmost importance. In some cases, the elimination of redundant structures provides greater flexibility of placement, positioning, and surgical implantation procedures. The relatively simple design also reduces the cost of goods sold (COGS) and provides other technical advantages like reduced risk of failure and easier manufacturability.

FIG. 4 shows a receiver generally designated 20. The receiver 20 can be, for example, an implantable receiver of a TET system and can be configured to receive wireless power from an external transmitter of the TET system. The receiver can include a receiver coil and electronics enclosed within a housing 25. Although these components are not shown in FIG. 4, a schematic representation of the receiver circuitry can be found in FIG. 1. The housing may be hermetically sealed. The housing may be fluid tight. The receiver can include, but is not necessarily limited to, a receiver circuit, tuning circuit, signal processing circuit, power source (e.g. batteries, such as lithium-ion batteries), and controls (none of which are shown in FIG. 4). The receiver can also include a number of wire turns that may be all in one solenoidal layer or distributed over multiple layers.

The housing 25 includes an enclosure covered with a covering 40 formed of magnetically susceptible material. In an exemplary embodiment, the housing is formed of a metal and the covering is formed of ferrite. The housing may be formed of a variety of materials. The covering does not need to be formed of a purely ferrite materials. In various embodiments, the housing is covered in a ferrite-based material and/or alloy. As used herein, "ferrite" refers to materials with a significant ferrimagnetic or ferromagnetic component (percent by weight).

In one embodiment, the covering 40 of housing 25 comprises a plurality of ferrite tiles 41. One will appreciate that the housing may be only partially covered in other embodiments. The tiles may all be of a uniform size, or may be of different sizes. In the embodiment shown in FIG. 4, the tiles 41 on the top/bottom portions 30 of the housing 25 can be, for example, rectangular. The tiles 41 on the sides 33 of the housing 25 can be, alternatively, square shaped. It should be understood that any number of shape of tiles can be used to cover the housing 25. For example, a tile could be custom manufactured to precisely cover one face of the housing. Also referring to FIG. 4, there may exist small gaps 35 between the ferrite tiles 41, particularly near the edges of the housing. These gaps can be minimized or eliminating by arranging the tiles 41 on one side of the enclosure (e.g., top/bottom portion 30) so as to overlap the edges of the tiles 41 on the adjacent side of the enclosure (e.g., side 33).

The surface area of the housing that is covered may depend upon design goals and expected use. The thickness of the exemplary ferrite tiles is sufficient such that the magnetization of the ferrite is not saturated. In many implementations, the ferrite is far from saturation, and the thickness is instead chosen to be practical during manufacture, e.g., the ferrite tiles are not so thin that they could easily crack or break apart during the assembly process.

Housing 25 is intended to be wrapped with windings to form receiver 20. In various embodiments, the housing is wrapped end-to-end with Litz wires. The housing may have a plurality of turns, for example, 5 turns, 10 turns, 15 turns, 20 turns, 25 turns, or more.

FIGS. 5 and 6 illustrate use of two different receiver configurations in accordance with various aspects of the invention. FIG. 5 is a cross-sectional schematic representation of a receiver without a ferrite covering. FIG. 6 is a cross-sectional schematic representation of a receiver with a ferrite covering similar to FIG. 4.

FIG. 5 illustrates interaction of a receiver 10 with flux lines when it is introduced into a field of the transmitter (e.g., the transmitter of FIG. 1). Receiver 10 includes a housing 13 without a ferrite covering. Flux lines F1, F2, F3, and F4 are presented to receiver 20. Lines F1 and F2 pass through a front face and exit out a back face of the receiver. Lines F1 and F2 induce a good electromagnetic force (voltage) in the receiver coil. Lines F1 and F2 are said to be efficient because they are picked up by all the windings. Line F3 passes through the front face and out the sidewall. F3 is relatively efficient in that it is picked up by most of the windings. In the illustrated embodiment, for example, voltage is induced in about half the windings. Line F4 presents a more significant problem. Line F4 passes through the front face and out the front edge of sidewall such that it only passes through a small percentage of the turns. In the case of FIG. 5, line F4 induces a voltage in only one or two turns.

Turning to FIG. 6, a receiver 20 including a housing 25 a ferrite covering 40. The ferrite-covered housing can be wrapped with wires 22 in a plurality of turns.

In contrast to receiver 10 of FIG. 5, receiver 20 in FIG. 6 more efficiently translates the flux lines into an induced voltage. Receiver 20 also shields the components inside housing 25 from interference by the magnetic field lines.

Lines F1' and F2' induce a voltage in all the wires similar to the example of FIG. 5. Unlike the structure above, however, lines F3' and F4' create larger voltages in the receiving coil than similar lines F3 and F4 with receiver 10. Line F3' hits housing 25 along a front face. The magnetic properties of the material cause the energy to travel from the point of impact along the front face and sidewall and exit somewhere further past the turns. This is in contrast to the example of F3 where the line travels directly through the structure. In the example of FIG. 6, the line is picked up by most of the turns whereas without the ferrite covering shown in FIG. 5 the same line would only be picked up by about half the turns. Similarly, line F4' is picked up by a larger number of the turns than would be the case with the structure of FIG. 5. In turn, ceteris paribus, a greater voltage is created when the receiver is introduced to the same field. The structure is thus said to be more efficient. Efficiency is represented herein as $\eta$ (eta).

Figure 7:
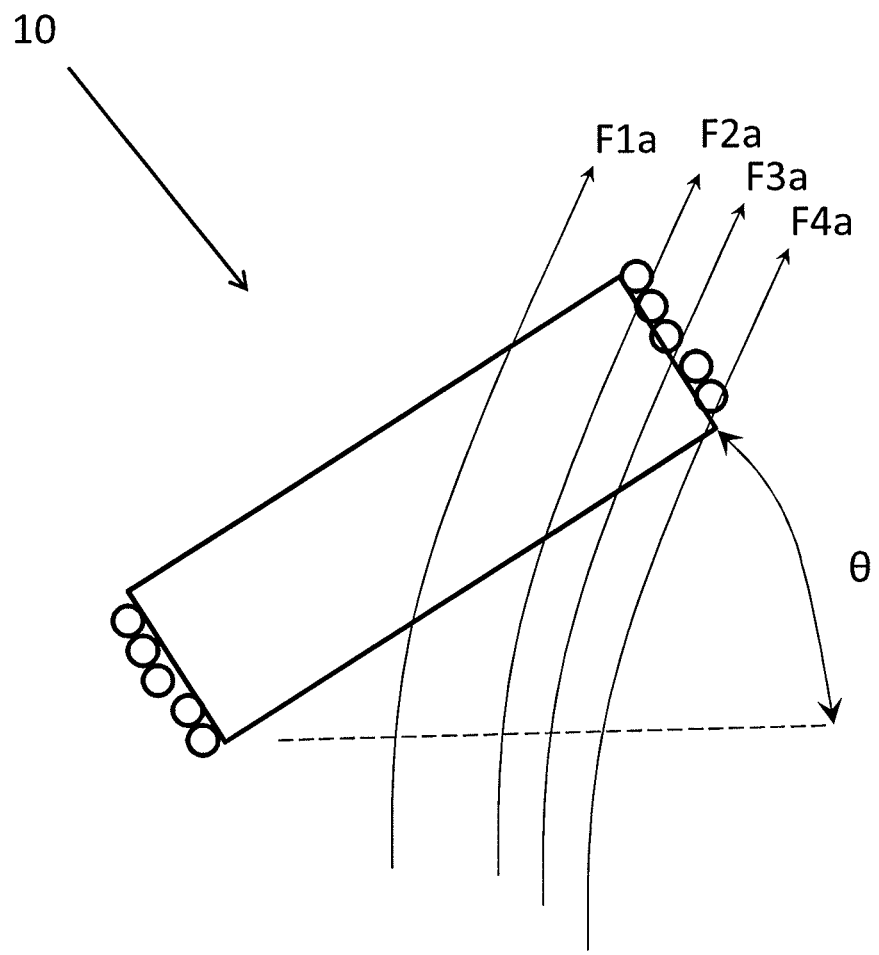
FIG. 7 is a cross-sectional, schematic view of the receiver of FIG. 5, illustrating the receiver turned at an angle θ.
Figure 8:
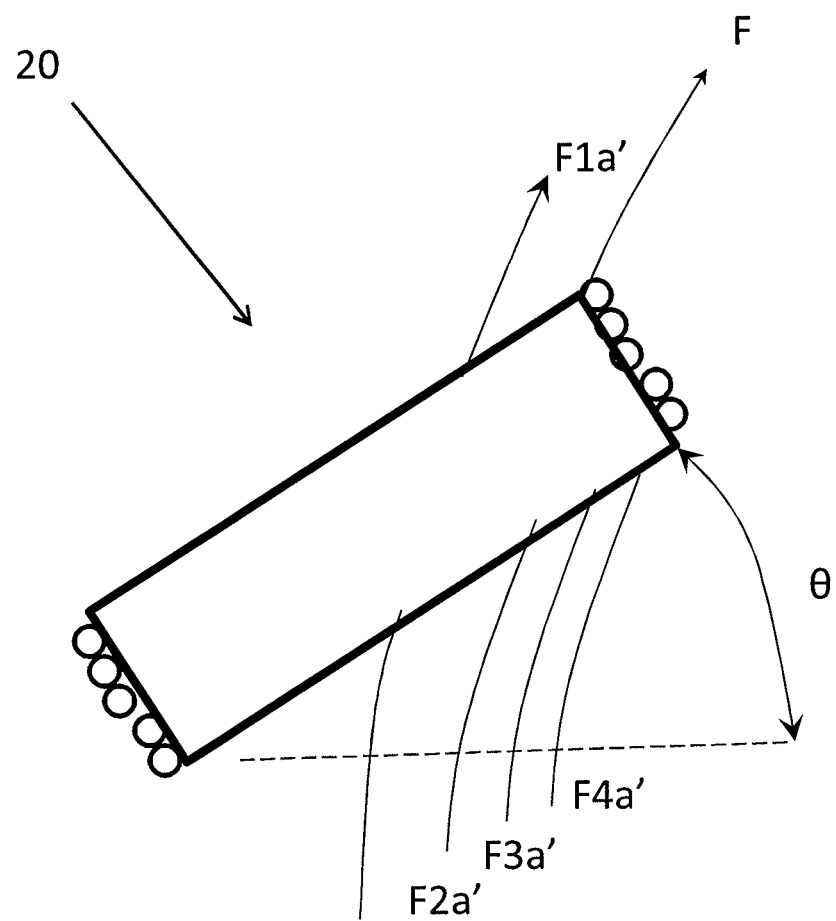
FIG. 8 is a cross-sectional, schematic view of the receiver of FIG. 6, illustrating the receiver turned at an angle θ.

The improved efficiency of receiver 20 is more pronounced as the angle $\theta$ (theta) of the receiver changes relative to the transmitter. FIGS. 7 and 8 illustrate how the same flux lines are redirected using the ferrite covering to improve efficiency. FIG. 7 shows the same receiver 10 of FIG. 5 except the receiver has been rotated at an angle $\theta$. In this exemplary case lines F2a, F3a, and F4a all pass through the interior of the receiver housing and out a sidewall. Thus, the efficiency is diminished for these lines and the lines also interfere with the internal components. By contrast, receiver 20 of FIG. 8 generates more voltage in the same field and reduces or eliminates interference with internal components. Lines F2a', F3a', and F4a' are all guided around the housing periphery and are transferred away from the housing further back along the windings as line F.

Figure 9:
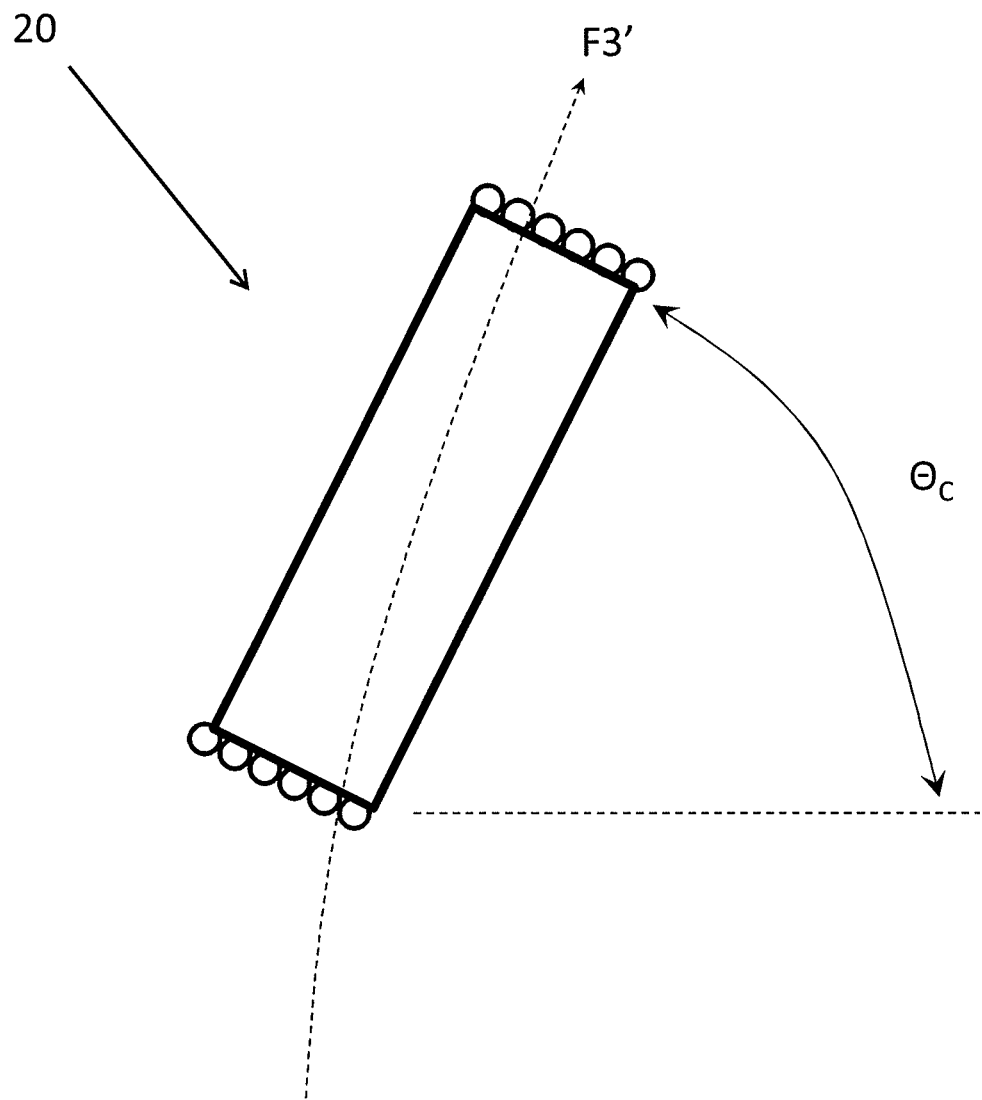
FIG. 9 is a cross-sectional, schematic view of the receiver of FIG. 6, illustrating the receiver turned at an angle $θ_C$.

With the receiver 20 making use of a covering 40, the improvements in efficiency may be lost at a particular critical angle, $\theta_C$. FIG. 9 shows receiver 20 at an angle $\theta_C$. In the illustrated embodiment, line F3' passes through one sidewall and out another sidewall. Indeed, more lines enter the first sidewall than the front face because of the steep angle. In other words, the surface area in a plane parallel the transmitter is larger for the sidewall than the front face. At angles beyond $\theta_C$, some field lines are redirected by the ferrite so that they are picked up by fewer turns than in a receiver without ferrite.

Figure 10:
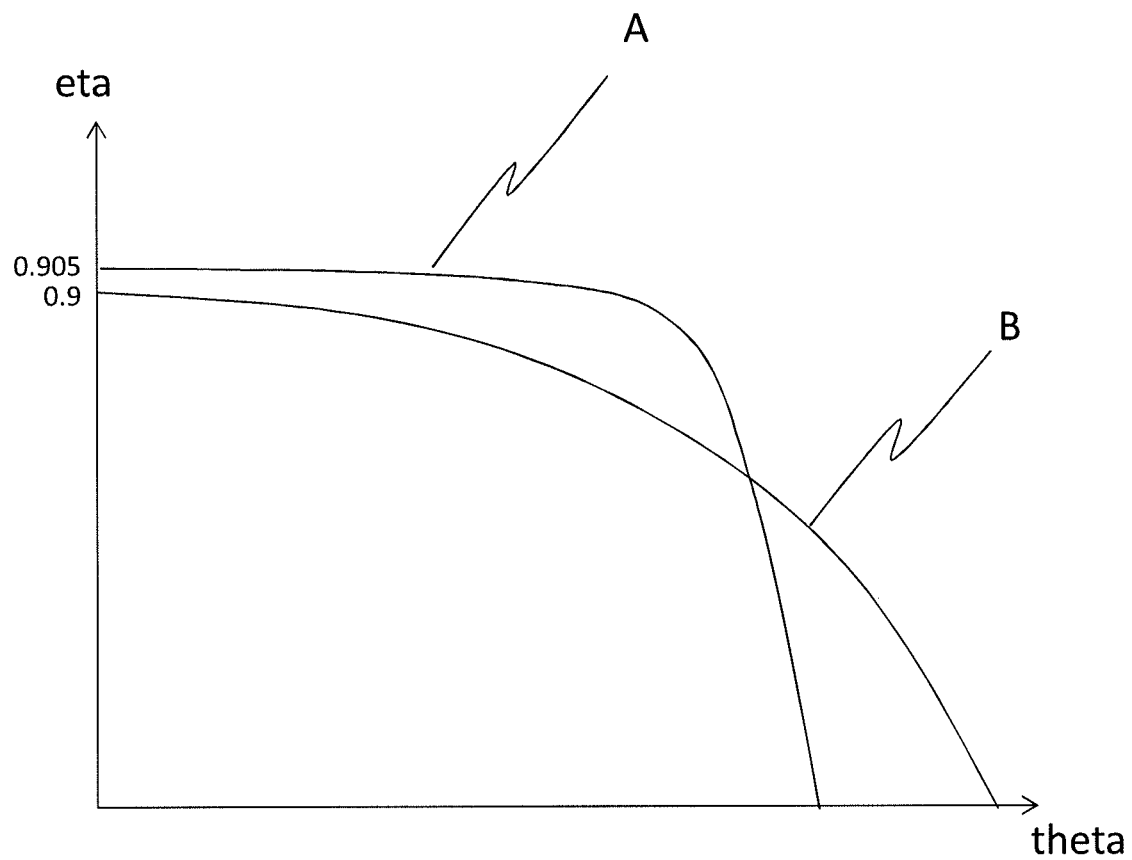
FIG. 10 is a graph illustrating efficiency of two receivers A and B at varying angles θ, receiver A having a ferrite covering and receiver B without a ferrite covering.

FIG. 10 is a graph illustrating the effect described above with respect to FIGS. 5-9. Line A illustrates data obtained using a structure similar to that of receiver 20, with a ferrite covering. Line A illustrates data obtained using a structure similar to that of receiver 10, without the covering. The graph illustrates that when the receiver and transmitter are perfectly aligned (i.e. parallel) the efficiency of receiver 20 is slightly higher. In one case the efficiency was found to be about 0.5% higher.

Moving along the curves, the efficiency of receiver 20 remains high over a far wider range of angles than receiver 10. This is shown by the flatter section of line A versus the declining slope of line B. At some angle there is an inflection point where the slope of line A rapidly changes. This effect is described above with respect to FIG. 9. Slightly beyond this angle lines A and B intersect and the structure of receiver 10 becomes more efficient.

Lines A and B approach the x-axis, theta, at different points. This shows that the efficiency of receiver 20 drops to zero at a smaller angle than receiver 10.

Figure 11:
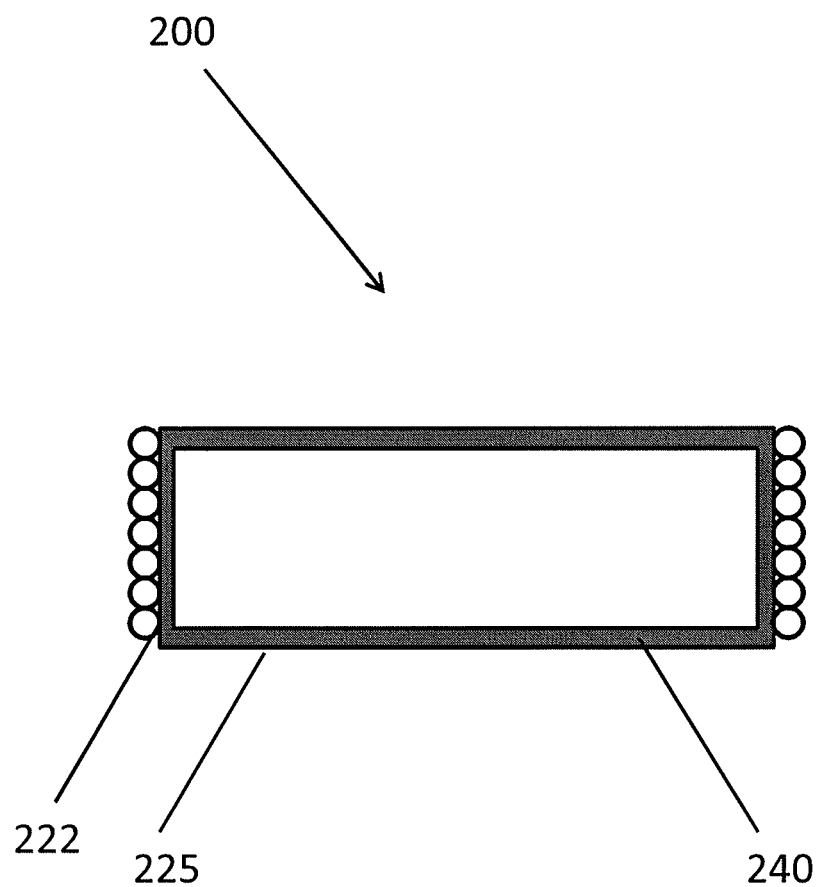
FIG. 11 is a cross-sectional, schematic view of an exemplary receiver, the receiver including a continuous ferrite covering in accordance with various aspects of the invention.

FIG. 11 shows a receiver 200 similar to receiver 20 except the covering is formed of a material that coats the housing. The material defines a covering 240 around a housing 225 and wrapped by wire turns 222. Covering 240 may be formed by dip coating or similar processes. The exemplary covering does not include gaps as would be present with tiles. Moreover, the covering 240 can be relatively thicker than covering 40.

One will appreciate from the description herein how to select the components to optimize performance based on a particular application. In various embodiments, the receiver can be configured to make use of the flat section of line A. For example, the receiver can be configured such that the critical angle, $\theta_C$, is greater than the largest angle expected to be seen in practice. In this manner the receiver will operate efficiently across the entire operational range of angles. In another example, the inflection point may be used such that little or no voltage is induced beyond a certain angle. The system could recognize a sharp drop in voltage and perform an action (e.g. generate an alarm or fault code). For example, the system can send an audible or visible alarm to the user that the coils are drastically out of alignment.

One aspect of the disclosure is directed to an implantable receiver for wirelessly receiving energy from a transmitter, including a housing enclosing volume including a receiving coil and components susceptible to interference by magnetic flux; a covering around at least a portion of the housing; at least one wire wrapped around the housing to form a plurality of turns; wherein the covering is formed of a ferrite material configured to both magnetically shield a respective portion of the internal volume and redirect incoming magnetic flux.

In various embodiments, the receiver includes coil circuitry including at least two coils; and receiver circuitry configured to transmit power excited in the receiver coil in response to exposure to a field to a load. In various embodiments, the load is an implantable medical device including an operative component. The operative component may be a circulatory support device. The operative component may be a blood pump for supporting and/or replacing the function of the heart. The operative component may be a left ventricular assist device, right ventricular assist device, bi-ventricular assist device, and/or total artificial heart. All or part of the operative component may be external to the body.

In various embodiments, the covering comprises a plurality of tiles. In various embodiments, the covering covers the entire housing periphery.

Various aspects of the invention are directed to a system including a receiver, a transmitter for generating a magnetic field to the receiver, and an implantable mechanical circulatory support (MCS) device. In various embodiments, the MCS device is configured to be powered by energy from the receiver. In various embodiments, the system further includes an implantable battery. In various embodiments, the MCS device is configured to be powered by one of the receiver, the battery, or a combination thereof. In various embodiments, the system further includes an implantable controller.

Another aspect of the disclosure is directed to a method of using the system, and in particular the receiver. In various respects the disclosure is directed to wirelessly transmitting energy comprising energizing a transmitter to generate a magnetic field, and positioning the receiver in the magnetic field to induce a voltage in the receiver coil. In various embodiments, the method includes positioning the receiver in a mammalian body. In various embodiments, the method includes positioning the receiver in a patient suffering from heart failure, cardiogenic shock, or undergoing high risk surgery (e.g. percutaneous coronary intervention). In various embodiments, the method includes positioning the receiver in the chest cavity of a human.

One will appreciate from the description herein that the configuration of the covering may be modified to improve performance. For example, only a portion of the housing may be covered with ferrite material to achieve a desired efficiency-angle curve. In one example, only a portion of the housing is covered based on what part of the housing is desired to be magnetically shielded. These and many other modifications are within the spirit of the inventions.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. An implantable receiver configured to receive wireless energy, comprising:
   a metal housing defining an interior space containing internal components; and
   a covering that covers at least two sides of the metal housing, the covering being formed of a ferrite material, wherein the covering includes a first set of tiles covering a top portion of the metal housing and a second set of tiles covering a side of the metal housing, wherein each tile included in the first set of tiles and the second set of tiles includes a plurality of edge faces, an inner face facing the metal housing, and an outer face opposite the inner face, wherein the outer face of each tile has a larger surface area than each edge face of that tile, wherein the outer face of each tile of the first set of tiles faces a first direction, and wherein the outer face of each tile of the second set of tiles faces a second direction perpendicular to the first direction.

2. The receiver of claim 1, wherein the internal components include receiver circuitry configured to transmit power to a load in response to an incoming magnetic flux.

3. The receiver of claim 2, wherein the load is an implantable medical device including an operative component.

4. The receiver of claim 3, wherein the operative component is a circulatory support device.

5. The receiver of claim 3, wherein the operative component is a blood pump.

6. The receiver of claim 1, wherein the covering covers an entire periphery of the metal housing.

7. The receiver of claim 1, wherein the covering redirects incoming magnetic flux from an external transmitter towards a receiver coil to improve power transfer efficiency.

8. The receiver of claim 1, wherein the first set of tiles have a different shape than the second set of tiles.

9. The receiver of claim 8, wherein the first set of tiles are rectangular and the second set of tiles are square shaped.

10. The receiver of claim 1, wherein the first set of tiles are adjacent one another.

11. The receiver of claim 1, wherein a first tile on the top portion of the metal housing overlaps an edge face of a second tile on the side of the metal housing to eliminate gaps between the first tile and the second tile.

12. The receiver of claim 1, wherein the receiver further includes at least two wires wrapped around the housing to form a receiver coil.

13. A method of improving efficiency in a wireless power transfer system, comprising:
   generating magnetic flux with a transmitter towards a receiver; and
   directing the magnetic flux towards a receiver coil of the receiver, the receiver including a ferrite covering that covers at least two sides of a metal housing of the receiver, the covering including a first set of tiles disposed on a top portion of the metal housing and a second set of tiles disposed on a side of the metal housing, wherein each tile included in the first set of tiles and the second set of tiles includes a plurality of edge faces, an inner face facing the housing, and an outer face opposite the inner face, wherein the outer face of each tile has a larger surface area than each edge face of that tile, wherein the outer face of each tile of the first set of tiles faces a first direction, and wherein the outer face of each tile of the second set of tiles faces a second direction perpendicular to the first direction.

14. The method of claim 13, wherein a first tile on the top of the housing overlaps an edge face of a second tile on the side of the housing to eliminate gaps between the first tile and the second tile.

15. The method of claim 13, wherein the first set of tiles have a different shape than the second set of tiles.

16. The method of claim 15, wherein the first set of tiles are rectangular and the second set of tiles are square shaped.

17. The method of claim 13, wherein the first set of tiles are adjacent one another.

18. The method of claim 13, wherein the receiver is implanted in a patient.

* * * * *